United States Patent
Sardo (12)

(10) Patent No.: US 6,221,414 B1
(45) Date of Patent: Apr. 24, 2001

(54) PROCESS FOR TREATING FRUITS AND VEGETABLES AFTER HARVESTING, WITH PURIFICATION OF PLANT-PROTECTION PRODUCTS CONTAMINATED WITH AROMATIC PRIMARY AMINES

(75) Inventor: Alberto Sardo, Chateaurenard (FR)

(73) Assignee: Xeda International, Saint-Andiol (FR)

( * ) Notice: Subject to any disclaimer, the term of this patent is extended or adjusted under 35 U.S.C. 154(b) by 0 days.

(21) Appl. No.: 09/384,286

(22) Filed: Aug. 27, 1999

(30) Foreign Application Priority Data

Sep. 2, 1998 (FR) .................................................. 98 10980

(51) Int. Cl.$^7$ .................................................. A23L 3/3463
(52) U.S. Cl. .................... 426/321; 426/102; 426/615; 564/307; 564/433; 564/435; 564/437
(58) Field of Search ..................... 426/321, 615, 426/102; 564/433, 307, 435, 437

(56) References Cited

U.S. PATENT DOCUMENTS

| | | | |
|---|---|---|---|
| 3,526,519 | * 9/1970 | Kleiman | 426/321 |
| 5,602,284 | * 2/1997 | Arndt et al. | 564/433 |
| 5,709,800 | 1/1998 | Ross et al. | 210/762 |

FOREIGN PATENT DOCUMENTS

| | | |
|---|---|---|
| 0084285 | 7/1983 | (EP) . |
| 2689506 | 10/1993 | (FR) . |
| 1009064 | * 6/1998 | (NL) . |

OTHER PUBLICATIONS

Chemical Abstracts, vol. 82, No. 21, May 26, 1975, Columbus, Ohio, US; abstract No. 139552.

* cited by examiner

*Primary Examiner*—Helen Pratt
(74) *Attorney, Agent, or Firm*—Wenderoth, Lind & Ponack, L.L.P.

(57) ABSTRACT

The invention relates to a process for treating fruit and vegetables after harvesting, using, as plant-protection treatment composition, the mixture with water of the reaction medium resulting from the implementation of steps of purification of a plant-protection product contaminated with impurities of aromatic primary amine type. The process contains the steps of:

a) the placing in contact with stirring, at a temperature between 15 and 25° C., of an aqueous solution of an alkali metal nitrite with an organic solution prepared by dissolving the said plant-protection product to be purified in a solvent chosen from a nonionic surfactant, a $C_2$–$C_{12}$ glycol and mixtures thereof;

b) the addition of a strong inorganic acid to the resulting reaction medium, while stirring at the said temperature;

c) followed by heating of the reaction medium to a temperature of between 30 and 70° C.

20 Claims, No Drawings

PROCESS FOR TREATING FRUITS AND VEGETABLES AFTER HARVESTING, WITH PURIFICATION OF PLANT-PROTECTION PRODUCTS CONTAMINATED WITH AROMATIC PRIMARY AMINES

The present invention relates to a simplified process for purifying plant-protection products contaminated with impurities of aromatic primary amine type.

Many plant-protection products commonly used in the treatment of fruit and vegetables are contaminated, in their commercial form, with undesirable toxic substances. This is the case especially for diphenylamine, which is widely used on account of its antioxidant properties, which is contaminated with various manufacturing side products, in particular primary aromatic amines such as aniline, 4-aminobiphenyl and 2-aminobiphenyl.

This is also the case for ethoxyquine, an antioxidant product, which is contaminated with p-phenetidine. Mention may also be made of chlorprofam which is a potato anti-germinating agent and which contains appreciable amounts of meta-chloroaniline.

FR 2,689,506 describes a process for selectively eliminating primary amines contaminating diphenylamine, by placing a solution of contaminated diphenylamine in contact with a cationic ion-exchange resin in the presence of water. Although effective, this process is complex and laborious. It requires either the use of columns packed with ion-exchange resin or the separation of the ion-exchange resin from the reaction medium before treatment of the fruit and vegetables.

The process of the invention does not have these drawbacks. Specifically, according to the invention, the reaction medium recovered after the process can be used directly for the preparation of a plant-protection composition intended for the treatment of fruit and vegetables. The use of the process of the invention is also particularly simple and requires no sophisticated or expensive apparatus.

The process claimed is directed towards freeing a given plant-protection product of its impurities of aromatic primary amine type. The process of the invention is effective irrespective of the exact nature and the amount of the said impurities of aromatic type. It is particularly suitable for the elimination of the impurities of formula I:

$$\text{Ar—NH}_2 \qquad \qquad \text{I}$$

in which Ar represents a monocyclic or polycyclic aromatic nucleus optionally substituted with one or more radicals chosen from a halogen atom; a $(C_1-C_8)$alkyl or $(C_1-C_8)$ alkoxy group; and amino.

The term "alkyl group" means a linear or branched hydrocarbon chain. Preferably, the said alkyl group comprises from 1 to 5 carbon atoms.

The alkyl part of the alkoxy group is defined similarly.

In a particularly advantageous manner, the aromatic nucleus Ar is mono- or bicyclic. Examples which may be mentioned are phenyl, naphthyl, anthryl and phenanthryl groups, phenyl and naphthyl groups being preferred.

The process of the invention is particularly suitable for the purification of plant-protection products comprising up to 10,000 ppm by weight of impurities of aromatic primary amine type, preferably up to 1000 ppm.

The process of the invention consists in treating, in acid medium, the plant-protection product with an alkali metal nitrite, such as sodium nitrite or potassium nitrite.

More specifically, the process of the invention comprises:
a) the placing in contact with stirring, at a temperature between 15 and 25° C., of an aqueous solution of the said alkali metal nitrite with an organic solution prepared by dissolving the said plant-protection product to be purified in a solvent chosen from a nonionic surfactant, a $C_2-C_{12}$ glycol and mixtures thereof;
b) the addition of a strong inorganic acid to the resulting reaction medium, while stirring at the said temperature;
c) followed by heating of the reaction medium to a temperature of between 30 and 70° C.

The first and second steps of the process claimed are generally performed in the order indicated. However, it is possible, in the context of the invention, to acidify the aqueous alkali metal nitrite solution in a first step, and then place the said acidified aqueous solution in contact with the organic solution of the plant-protection product, with stirring, before heating the reaction medium to a temperature of between 30 and 70° C.

It should be understood, however, that the embodiment which consists in carrying out steps a) and b) in the order indicated (step a) and then step b)) is preferred.

The aqueous alkali metal nitrite solution is preferably an aqueous solution containing 0.5 to 3 mol/liter of alkali metal nitrite, better still from 0.5 to 1.5 mol/liter, for example a molar solution.

The amount of the said aqueous solution used in step a) depends on the amount of impurities of primary aromatic amine type contained in the organic solution of the plant-protection product.

Strictly speaking, a stoichiometric amount of the alkali metal nitrite relative to the total number of moles of aromatic primary amino groups present in the organic solution is sufficient for total removal of the impurities. It will be noted that a given impurity can contain more than one aromatic primary amino group. This is the case in particular for the impurities of formula Ar—$NH_2$, in which Ar represents an aromatic nucleus substituted with more than one amino group.

However, it is desirable to use an excess of alkali metal nitrite. An amount ranging between 1 and 5 molar equivalents of the alkali metal nitrite relative to the total number of moles of aromatic primary amino groups, for example between 1 and 3 molar equivalents, is appropriate.

The organic solution of the plant-protection product is prepared by dissolving the plant-protection product in a solvent which is chosen from a nonionic surfactant, a $C_2-C_{12}$ glycol and mixtures thereof in any proportion.

According to the invention, it is nevertheless preferred for the said solvent to consist:
  of one or more nonionic surfactants;
  or of a mixture of one or more nonionic surfactants with one or more $C_2-C_{12}$-glycols.

Advantageously, the said solvent consists of one or more nonionic surfactants.

In the context of the invention, the term "glycols" means dihydroxylated alcohols derived from aliphatic hydrocarbons by replacement of two hydrogen atoms with two hydroxyl groups.

According to the invention, $C_2-C_6$ glycols are preferred, and in particular ethylene glycol and propylene glycol. Examples of nonionic surfactants which can be used according to the invention are, in particular:

the product of condensation of an aliphatic fatty alcohol, preferably a $C_8-C_{22}$ aliphatic fatty alcohol, with a $C_2-C_3$ alkylene oxide. The $C_2-C_3$ alkylene oxide can be ethylene oxide, propylene oxide or a mixture of ethylene oxide and propylene oxide in any proportion. An example of such surfactants is the product of condensation of lauryl alcohol (or n-dodecyl alcohol) with 30 mol of ethylene oxide;

the product of condensation of an alkylphenol in which the alkyl chain is $C_8$–$C_{22}$ with a $C_2$–$C_3$ alkylene oxide. Here also, the products of condensation with ethylene oxide, propylene oxide or a mixture of ethylene oxide and propylene oxide in any proportion are again advantageous. As examples of such surfactants, mention may be made of the product of condensation of n-nonylphenol with 10 mol of ethylene oxide;

the product of condensation of a fatty acid, preferably a $C_8$–$C_{22}$ fatty acid, with a $C_2$–$C_3$ alkylene oxide, for example ethylene oxide or propylene oxide or a mixture of ethylene oxide and propylene oxide in any proportion. These condensation products have an alkoxylated chain on the hydroxyl function of the carboxylic group. Preferred surfactants of this group are the condensation products obtained from oleic acid, palmitic acid and stearic acid.

Usually, the surfactants used result from the condensation of a fatty alcohol, a fatty acid or an alkylphenol with 3 to 50 mol of $C_2$–$C_3$ alkylene oxide.

Among the surfactants mentioned above, those with an HLB (hydrophilic-lipophilic balance) constant of between 6 and 18 are particularly preferred.

The organic solution used in step a) preferably comprises from 5 to 50% by weight of the said plant-protection product, better still from 10 to 30% by weight.

The aqueous solution is placed in contact with the organic solution of the plant-protection product at a temperature of between 15 and 25° C., with stirring.

In step b), the inorganic acid is a strong acid; in any case, an acid stronger than $HNO_2$ is desirable. Examples of such acids are sulphuric acid and hydrochloric acid.

The amount of strong acid which needs to be used is generally between 1.5 and 3.5 molar equivalents, relative to the amount of alkali metal nitrite used; preferably, two equivalents of strong acid are used.

The strong inorganic acid can be added to the reaction mixture in pure form or in the form of a dilute aqueous solution. Preferred dilute aqueous solutions are solutions from 0.5 to 3 N, better still from 0.5 to 1.5 N, for example 1 N.

In step c), the reaction mixture is stirred and heated at a temperature of between 30 and 70° C., preferably between 40 and 50° C., for the time required for total removal of the impurities of aromatic primary amine type.

A person skilled in the art may, for example, monitor the progress of the reaction by taking aliquots of the reaction medium at regular intervals and analysing them.

Generally, the reaction is complete after 30 minutes to 5 hours, or even 30 minutes to 3 hours.

In a particularly advantageous manner, the reaction medium resulting from the implementation of the process of the invention can be used directly, after addition of water, for the treatment of fruit and vegetables after harvesting. Depending on the nature of the plant-protection product present in the reaction medium, the treatment will have an antioxidant effect, an anti-germinating effect (anti-sprouting effect) on potato, and/or a fungicidal effect.

Thus, according to another of its aspects, the invention relates to a process for treating fruits and vegetables after harvesting, characterized in that the reaction medium resulting from the implementation of the process of the invention, mixed with water, is used as plant-protection treatment composition.

A first preferred embodiment of the invention consists in dispersing the reaction medium, obtained after implementing the process of the invention, in water before use. The dispersion is prepared preferably using an amount of water such that the ratio by volume of the reaction medium to water is between 1/100 and 1/1000, preferably between 1/50 and 1/1000. With this aim, the crude reaction medium can be stored and sold in its native form, in the form of an emulsifiable concentrate.

A second preferred embodiment of the invention consists in adding up to 30% by weight of water to the reaction medium. The resulting composition is particularly suitable for treating fruit and vegetables by spraying. In this case, the plant-protection composition can be stored, after addition of water to the reaction medium, in the form of a sprayable aerosol composition.

When it is envisaged to use the reaction medium for the preparation of an aerosol plant-protection composition, it is advantageous to use, in step a), a mixture of one or more nonionic surfactants and one or more glycols as solvent.

As a variant, since the solvent consists of one or more nonionic surfactants, it is recommended to incorporate one or more co-solvents chosen from $C_1$–$C_{12}$ aliphatic alcohols into the organic solution.

More generally, it is possible according to the invention to prepare the organic solution used in step a) by (i) dissolving the plant-protection product in a solvent and then (ii) adding one or more co-solvents chosen from $C_1$–$C_{12}$ aliphatic alcohols.

Advantageously, the plant-protection treatment composition used for treating fruits and vegetables comprises 5 to 50% by weight of the plant-protection product, 0 to 80% by weight of nonionic surfactants, 0 to 80% by weight of glycols, 0 to 20% by weight of aliphatic alcohols and 0 to 30% by weight of water.

More preferably, the said composition comprises 5 to 50% by weight of the plant-protection product, 5 to 80% by weight of nonionic surfactants, 0 to 60% by weight of glycols, 0 to 20% by weight of aliphatic alcohols and 0 to 30% by weight of water.

The plant-protection composition is obtained by carrying out the steps consisting in:

preparing an aqueous solution A of an alkali metal nitrite;

preparing an organic solution B by dissolving the plant-protection product in a solvent as defined above and, if necessary, adding one or more co-solvents (chosen from $C_1$–$C_{12}$ aliphatic alcohols);

placing solution A in contact with solution B, with stirring, at a temperature between 15 and 25° C.;

adding a strong inorganic acid to the resulting reaction medium, while stirring at the said temperature;

heating the reaction medium to a temperature between 30 and 70° C.; and adding water to the resulting reaction medium.

Preferably, the organic solution of the plant-protection product used in step a) thus essentially comprises from 5 to 50% by weight of the said plant-protection product; from 0 to 80% by weight, preferably from 5 to 80% by weight, of nonionic surfactants; from 0 to 80% by weight, preferably from 0 to 60% by weight, of $C_2$–$C_{12}$ glycols; and from 0 to 20% by weight of $C_1$–$C_{12}$ aliphatic alcohols.

According to another embodiment of the invention, it is possible to add various constituents to the plant-protection treatment composition, such as waxes, in order to apply it to fruit and vegetables. Such constituents are those commonly used in the technical field.

The invention is not intended to be limited to the purification of only one plant-protection product, but also encompasses the concomitant purification of several plant-protection products whenever each of these products contains impurities of aromatic primary amine type. In this case, an organic solution of the various plant-protection products should be prepared in order to carry out step a) of the process of the invention.

The process of the invention is more particularly suitable for the purification:

of diphenylamine which is contaminated in particular with aniline, 2-aminobiphenyl and 4-aminobiphenyl;

of chlorprofam which is contaminated in particular with meta-chloroaniline;

of ethoxyquine which is contaminated in particular with p-phenetidine.

In the following text, the invention will be described with reference to the examples which follow.

EXAMPLE 1

Purification of diphenylamine Contaminated with 300 ppm of aniline and 50 ppm of a Mixture of 2-aminobiphenyl and 4-aminobiphenyl An organic solution of 200 kg of diphenylamine in 800 kg of a mixture of the following three nonionic surfactants:

the product of condensation of oleic acid with 6 mol of ethylene oxide;

the product of condensation of oleic acid with 10 mol of ethylene oxide; and the product of condensation of n-nonylphenol with 10 mol of ethylene oxide, is prepared.

After complete dissolution of the diphenylamine in the mixture of surfactants, 1 kg of a 1 M sodium nitrite solution is added to the resulting solution.

After stirring for one hour, 2 kg of 1 M hydrochloric acid solution are added and the reaction medium is left stirring for a further 1 hour while heating at a temperature between 40 and 50° C.

HPLC (high performance liquid chromatography) analysis on an aliquot of the reaction medium is used to confirm that all of the contaminants of aromatic primary amine type have been removed.

The reaction medium is used after dispersion in water, as a treatment composition in the treatment of fruit and vegetables after harvesting. The treatment composition has the expected antioxidant and fungicidal effect.

EXAMPLE 2

Purification of chlorprofam Contaminated with 500 ppm of meta-chloroaniline

An organic solution of 200 kg of chlorprofam in 150 kg of a surfactant chosen from:

the product of condensation of n-dodecyl alcohol with 30 mol of ethylene oxide;

the product of condensation of n-nonylphenol with 10 mol of ethylene oxide; and mixtures thereof in any proportion, is prepared.

650 kg of propylene glycol are added to this solution.

After complete dissolution of the chlorprofam, 2 kg of aqueous 1 M sodium nitrite solution are added with stirring. After stirring for one hour, 4 kg of aqueous 1 M hydrochloric acid solution are added and the reaction medium is stirred for a further 1 hour while heating at a temperature between 40 and 50° C.

HPLC analysis on an aliquot of the reaction medium is then used to check that the meta-chloroaniline has been removed from the reaction medium.

The reaction medium is used, after addition of water, in the form of an aerosol composition which can be sprayed directly onto potatoes, and has the expected anti-germinating effect on potato.

What is claimed is:

1. Process for treating fruits and vegetables after harvesting, using, as a plant-protection treatment composition, a mixture with water of a reaction medium resulting from the implementation of steps of purification of a plant-protection product contaminated with impurities of aromatic primary amine type, the said steps comprising:

a) placing in contact with stirring, at a temperature between 15 and 25° C., an aqueous solution of an alkali metal nitrite with an organic solution prepared by dissolving the said plant-protection product to be purified in a solvent selected from the group consisting of a nonionic surfactant, a $C_2$–$C_{12}$ glycol and mixtures thereof;

b) addition of a strong inorganic acid to the resulting reaction medium, while stirring at the said temperature;

c) followed by heating of the reaction medium to a temperature of between 30 and 70° C.

2. Process according to claim 1, wherein the impurities of aromatic primary amine type have the formula $$Ar—NH_2 \qquad (I)$$

in which Ar is selected from the group consisting of a monocyclic or polycyclic aromatic nucleus and a monocyclic or polycyclic aromatic nucleus substituted with one or more radicals selected from the group consisting of a halogen atom; a $(C_1$–$C_8)$alkyl group; $(C_1$–$C_8)$alkoxy; and amino.

3. Process according to claim 1, wherein the plant-protection product is diphenylamine contaminated with impurities selected from the group consisting of aniline, 2-aminobiphenyl and 4-aminobiphenyl, and mixtures thereof.

4. Process according to claim 1, wherein the plant-protection product is chlorprofam contaminated with meta-chloroaniline.

5. Process according to claim 1, wherein the plant-protection product is ethoxyquine contaminated with p-phenetidine.

6. Process according to claim 1, wherein the said plant-protection product comprises up to 10,000 ppm by weight of impurities of aromatic primary amine type.

7. Process according to claim 1, wherein, in step c), the reaction medium is heated to a temperature between 40 and 50° C.

8. Process according to claim 1, wherein the nonionic surfactant is selected from the group consisting of a condensation product of a $C_8$–$C_{22}$ aliphatic fatty alcohol with a $C_2$–$C_3$ alkylene oxide; a condensation product of an alkylphenol in which the alkyl part is $C_8$–$C_{22}$ with a $C_2$–$C_3$ alkylene oxide; a condensation product of a $C_8$–$C_{22}$ fatty acid with a $C_2$–$C_3$ alkylene oxide; and mixtures thereof.

9. Process according to claim 1, wherein the said surfactant has an HLB (hydrophilic-lipophilic balance) constant of between 6 and 18.

10. Process according to claim 1, wherein the $C_2$–$C_{12}$ glycol is chosen from ethylene glycol and propylene glycol.

11. Process according to claim 1, wherein the said organic solution comprises from 5 to 50% by weight of the said plant-protection product.

12. Process according to claim 1, wherein the said strong inorganic acid is selected from the group consisting of hydrochloric acid and sulphuric acid.

13. Process according to claim 1, wherein the solvent used in step a) is a mixture of one or more nonionic surfactants.

14. Process according to claim 1, wherein the said organic solution also comprises one or more co-solvents selected from the group consisting of $C_1$–$C_{12}$ aliphatic alcohols.

15. Process according to claim 1, wherein the said organic solution consists of 5 to 50% by weight of the said plant-protection product, from 0 to 80% by weight of nonionic surfactants, from 0 to 80% by weight of $C_2$–$C_{12}$ glycols and from 0 to 20% by weight of $C_1$–$C_{12}$ aliphatic alcohols.

16. Process according to claim 1, wherein the plant-protection treatment composition is obtained by dispersing the said reaction medium in water, the ratio by volume of the reaction medium to water being between 1/50 and 1/1000.

17. Process according to claim 1, wherein the plant-protection treatment composition is obtained by adding up to 30% by weight of water to the reaction medium.

18. Process according to claim 1, wherein, in step a), the organic solution is obtained by dissolving the plant-protection product in a mixture of one or more nonionic surfactants and one or more glycols.

19. Process according to claim 1, wherein, in step a), the organic solution is obtained by dissolving the plant-protection product in a mixture of one or more nonionic surfactants and one or more co-solvents selected from the group consisting of $C_1$–$C_{12}$ aliphatic alcohols.

20. Process according claim 1, wherein the plant-protection product comprises up to 1000 ppm by weight of aromatic primary amine type.

* * * * *